US010329233B2

(12) United States Patent
Blair (10) Patent No.: US 10,329,233 B2
(45) Date of Patent: *Jun. 25, 2019

(54) CHEMICAL REDUCTION USING A CATALYST COMPRISING FRUSTRATED LEWIS PAIRS

(71) Applicant: University of Central Florida Research Foundation, Inc., Orlando, FL (US)

(72) Inventor: Richard G. Blair, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/472,009

(22) Filed: Mar. 28, 2017

(65) Prior Publication Data

US 2017/0197900 A1    Jul. 13, 2017

Related U.S. Application Data

(63) Continuation of application No. 14/650,546, filed as application No. PCT/US2013/073747 on Dec. 6, 2013, now Pat. No. 9,624,154.

(Continued)

(51) Int. Cl.
*C07C 51/00* (2006.01)
*B01J 27/24* (2006.01)
(Continued)

(52) U.S. Cl.
CPC .............. *C07C 51/00* (2013.01); *B01J 27/24* (2013.01); *B01J 35/002* (2013.01);
(Continued)

(58) Field of Classification Search
CPC ...... B01J 27/24; B01J 35/002; B01J 37/0036; C07C 51/00; C10G 2/50; C10G 3/00
See application file for complete search history.

(56) References Cited

U.S. PATENT DOCUMENTS 8,299,284 B2    10/2012  Stephan et al.
2012/0283340 A1  11/2012  O'Hare et al.

FOREIGN PATENT DOCUMENTS

DE    102009056970         6/2011
WO    WO-2011045605 A1 *   4/2011   ........... C07C 29/153

OTHER PUBLICATIONS

Choi, H. et al. J. Am. Chem. Soc. 2011, 133, 2084-2087 (Year: 2011).*

(Continued)

*Primary Examiner* — Medhanit W Bahta
(74) *Attorney, Agent, or Firm* — Dunlap Codding, P.C.

(57) ABSTRACT

The presently disclosed and/or claimed inventive concept(s) relates generally to the reduction of carbon dioxide by heterogeneous catalysis. More particularly, but not by way of limitation, the presently disclosed and/or claimed inventive concept(s) relates to the reduction of carbon dioxide by heterogeneous catalysis with a heterogeneous hydrogenation catalyst comprising structurally frustrated Lewis pairs, wherein, for example but not by way of limitation, formic acid is produced and hydrocarbons are indirectly produced. In one non-limiting embodiment, the heterogeneous catalyst comprises hexagonal boron nitride (h-BN) having structurally frustrated Lewis pairs therein.

19 Claims, 6 Drawing Sheets

Related U.S. Application Data (60) Provisional application No. 61/734,699, filed on Dec. 7, 2012.

(51) Int. Cl.
  *B01J 35/00* (2006.01)
  *C10G 3/00* (2006.01)
  *C10G 2/00* (2006.01)
  *B01J 37/00* (2006.01)

(52) U.S. Cl.
  CPC ............ *B01J 37/0036* (2013.01); *C10G 2/50* (2013.01); *C10G 3/00* (2013.01); *Y02P 30/20* (2015.11)

(56) References Cited

OTHER PUBLICATIONS

Peng, G. et al. J. Phys. Chem. 2012, 116, 3001-3006; published Dec. 26, 2011 (Year: 2012).*
Kang, H. S. J. Phys. Chem. B 2006, 110, 4621-4628 (Year: 2006).*
PCT/US2013/073749—WO/2014/089537—International Search Report and Written Opinion, dated Mar. 25, 2014, 10 pages.
Eros et al., "Expanding the Scope of Metal-Free Catalytic Hydrogenation through Frustrated Lewis Pair Design," Angewandte Chemie, vol. 49, pp. 6559-6563, Sep. 3, 2010.
Stepan et al., "Frustrated Lewis Pairs: Metal-free Hydrogen Activation and More," Angewandte Chemie International Edition, vol. 49, Issue 1, pp. 46-76, Jan. 4, 2010.
Lin et al., "Defect Functionalization of Hexagonal Boron Nitride Nanosheets," J. Phys. Chem. C., 2010, vol. 114, Issue 41, pp. 17434-17439, Web publication date Sep. 21, 2010 (Abstract Only).
PCT/US2013/073746—Extended European Search Report, dated Aug. 8, 2016, 12 pages.
PCT/US2013/073747—Extended European Search Report, dated Aug. 10, 2016, 9 pages.
Stephan, Douglas P., Frustrated Lewis Pairs: A New Strategy to Small Molecule Activation and Hydrogenation Catalysis, The International Journal for Inorganic, Organometallic and Bioinorganic Chemistry, Royal Society of Chemistry, GB, No. 17, p. 3129-3136, May 7, 2009.
Wang, P. et al., Hydrogen in Mechanically Prepared Nanostructured h-BN: A Critical Comparison with that in Nanostructured Graphite, Applied Physics Letters, AIP Publishing LLC, US, vol. 80, No. 2, p. 318-320, Jan. 14, 2002.
Wischert, Raphael, et al., [Gamma]—Alumina: The Essential and Unexpected Role of Water for the Structure, Stability, and Reactivity of "Defect" Sites, Journal of the American Chemical Society, vol. 134, No. 35, p. 14430-14449, Aug. 3, 2012.
Wu, et al., Metal Fee Hydrogenation Reaction on Carbon Doped Boron Nitride Fullerene: A DFT Study on the Kinetic Issue, International Journal of Hydrogen Energy, vol. 37, No. 19, p. 14336-14342, Oct. 1, 2012.

* cited by examiner

CHEMICAL REDUCTION USING A CATALYST COMPRISING FRUSTRATED LEWIS PAIRS

CROSS-REFERENCE TO RELATED APPLICATIONS/INCORPORATION BY REFERENCE STATEMENT

This application is a continuation of U.S. application Ser. No. 14/650,546, filed Jun. 8, 2015, which claims benefit of a national stage application filed under 35 U.S.C. 371 of PCT/US2013/073747, filed Dec. 6, 2013, which claims benefit under 35 U.S.C. 119(e) of U.S. Provisional Patent Application Ser. Nos. 61/734,699, filed Dec. 7, 2012, and 61/860,067, filed Jul. 30, 2013, the entire contents of each of which is hereby expressly incorporated herein by reference.

BACKGROUND

1. Field of the Inventive Concept(s)

The presently disclosed and/or claimed inventive concept(s) relates generally to the reduction of carbon dioxide by heterogeneous catalysis. More particularly, but not by way of limitation, the presently disclosed and/or claimed inventive concept(s) relates to the reduction of carbon dioxide by heterogeneous catalysis with a heterogeneous hydrogenation catalyst comprising structurally frustrated Lewis pairs, wherein, for example but not by way of limitation, formic acid is produced and hydrocarbons are indirectly produced. In one non-limiting embodiment, the heterogeneous catalyst comprises hexagonal boron nitride (h-BN) having structurally frustrated Lewis pairs therein.

2. Background of the Inventive Concept(s)

Carbon dioxide ($CO_2$), a well-known greenhouse gas, is the main product emitted by the combustion of hydrocarbons for the generation of power for many uses including electricity and transportation. In 2012, $CO_2$ production was at a record high of 31.6 gigatons, a number that will continue to escalate as consumer demands increase. As such, it is critically important to the environment to reduce the emissions of $CO_2$.

Existing approaches to reducing carbon dioxide emissions include sequestration, electrochemical reduction, and homogeneous reduction. However, each of these processes has specific disadvantages. For example, sequestration is limited to the space available to store $CO_2$, electrochemical reduction is energy intensive, and homogeneous reduction requires the utilization of catalysts that are sensitive to both air and moisture. Additionally, existing approaches generally use catalysts comprising precious metals such as palladium, platinum, nickel, and rhodium, which increases the cost of $CO_2$ reduction and depletes the supply of these precious metals. These and other factors make the presently disclosed and/or claimed process of using a heterogeneous hydrogenation catalyst, to not only reduce $CO_2$ emissions but also produce a commercially valuable product, an attractive alternative to existing approaches.

Frustrated Lewis Pair (FLP) catalysts are potentially useful as one type of heterogeneous hydrogenation catalyst. In 2007, Stephan and his team developed a chemical system capable of releasing and absorbing molecular hydrogen using frustrated Lewis pairs. (See *Frustrated Pairs*, in *Catalysis without Precious Metals*, M. R. Bullock, Editor. 2010, Wiley-VCH Verlag GmbH & Co. KGaA. P.I-XVIII, hereby incorporated in its entirety). Stephan determined that when a sterically encumbered Lewis acid approaches a bulky Lewis base, adduct formation is hindered and gives rise to electronic "frustration". Such frustration effectively mimics the donor-acceptor properties of transition metals. Stephan and his team demonstrated that upon exposure to 1 atm $H_2$ at 25° C., a solution of red phosphino-borane $[(C_6H_2Me_3-2,4,6)_2P(C_6F_4)BF(C_6F_5)_2]$ transformed to the colorless zwitterionic salt $[(C_6H_2Me_3-2,4,6)_2PH(C_6F_4)BH(C_6F_5)_2]$. Upon thermolysis at 150° C., the salt lost $H_2$ and converted back to the original phosphine-borane substrate. Such phosphonium borates (as well as similar compounds) have been shown to successfully catalyze the hydrogenation of select imines, enamines, aldehydes, and olefins.

However, to date, only homogeneous FLP catalytic systems have been studied, i.e., FLP catalysts and the resulting reactions have previously involved the FLP catalyst being in the same phase as the reactants. For example, the homogeneous FLP catalyst is typically co-dissolved in a solvent with the reactants. Heterogeneous catalysis, on the other hand, is performed with the catalyst in a different phase from that of the reactants. One example of heterogeneous catalysis is the petrochemical alkylation process where the liquid reactants are immiscible with a solution containing the catalyst. Heterogeneous catalysis offers the advantage that products may be readily separated from the catalyst. Typically, heterogeneous catalysts are more stable and degrade much slower than homogeneous catalysts.

As detailed in the presently disclosed and/or claimed invention, heterogeneous catalysts, e.g., heterogeneous FLP catalysts, can be used to hydrogenate the carbonyl bond of carbon dioxide to produce formic acid, which as of 2013 has a commodity price of 700-1,000 USD/metric ton and can be used as a fuel or in fuel cells. Additionally, formic acid can be thermally decomposed to produce carbon monoxide and water, wherein the carbon monoxide can be further converted to a hydrocarbon fuel using Fischer-Tropsch chemistry. Given that on average a typical power plant emits 10,000 tons of $CO_2$ per day, the ability to efficiently turn $CO_2$ into a commodity while reducing the emissions of $CO_2$ is a valuable alternative to processes currently available for industrial and commercial use.

In view of the foregoing, there is a need for a heterogeneous catalyst capable of chemically reducing $CO_2$ in order to efficiently decrease the production of $CO_2$ emissions. In particular, a heterogeneous hydrogenation catalyst having an FLP-type electronic structure would be a valuable addition to catalysts currently available for industrial and commercial use. It is to such a heterogeneous hydrogenation FLP catalyst and its method of use that the presently disclosed and/or claimed inventive concept(s) is directed.

SUMMARY OF THE INVENTIVE CONCEPTS

The presently disclosed and/or claimed inventive concept(s) relates generally to the reduction of carbon dioxide by heterogeneous catalysis with a heterogeneous hydrogenation catalyst comprising structurally frustrated Lewis pairs. At least one defect frustrates at least one pair of Lewis acid and Lewis base sites such that the frustrated pair of Lewis acid and Lewis base sites are catalytically active and promote hydrogenation. In one non-limiting embodiment, the heterogeneous catalyst comprises hexagonal boron nitride (h-BN) having structurally frustrated Lewis pairs therein. Methods of preparing and using the heterogeneous hydrogenation catalyst for chemically reducing $CO_2$ to produce, for example but without limitation, formic acid and hydrocarbon byproducts, are also taught and disclosed.

BRIEF DESCRIPTION OF THE DRAWINGS

Implementations of the presently disclosed and/or claimed inventive concept(s) may be better understood when consideration is given to the following detailed description thereof. Such description makes reference to the annexed pictorial illustrations, schematics, graphs, and drawings. The figures are not necessarily to scale and certain features and certain views of the figures may be shown exaggerated, to scale, or in schematic in the interest of clarity and conciseness.

DETAILED DESCRIPTION

Before explaining at least one embodiment of the presently disclosed and/or claimed inventive concept(s) herein in detail, it is to be understood that the presently disclosed and/or claimed inventive concept(s) is not limited in its application to the details of construction, experiments, exemplary data, and/or the arrangement of the components set forth in the following description, or illustrated in the drawings. The presently disclosed and/or claimed inventive concept(s) is capable of other embodiments or of being practiced or carried out in various ways. Also, it is to be understood that the phraseology and terminology employed herein is for purpose of description only and should not be regarded as limiting in any way.

In the following detailed description of embodiments of the presently disclosed and/or claimed inventive concept(s), numerous specific details are set forth in order to provide a more thorough understanding of the inventive concept(s). However, it will be apparent to one of ordinary skill in the art that the inventive concept(s) within the disclosure and/or appended claims may be practiced without these specific details. In other instances, well-known features have not been described in detail to avoid unnecessarily complicating the instant disclosure. Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the presently disclosed and/or claimed inventive concept(s) have been described in terms of preferred embodiments, it will be apparent to those skilled in the art that variations may be applied to the articles and/or methods and in the steps or in the sequence of steps of the method described herein without departing from the concept, spirit, and scope of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" may mean "one", but it is also consistent with the meaning of "one or more", "at least one", and "one or more than one". The use of the term "or" is used to mean "and/or" unless explicitly indicated to refer to alternatives only if the alternatives are mutually exclusive, although the disclosure supports a definition that refers to only alternatives "and/or". Throughout this application, the term "about" is used to indicate that a value includes the inherent variation of error for the quantifying device, the method being employed to determine the value, or the variation that exists among the study subjects. For example, but not by way of limitation, when the term "about" is utilized, the designation value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABC-CCC, CBBAAA, CABABB, and so forth. The skilled artisan will understand that typically there is no limit on the number of items or terms in any combination, unless otherwise apparent from the context.

References to hydrogenation of specific compounds herein are for exemplary purposes only, and the presently disclosed and/or claimed inventive concept(s) can be used with other hydrogenatable compounds. For example, the heterogeneous hydrogenation catalyst may be used to reduce or saturate organic compounds having alkyne, aldehyde, ketone, ester, imine, amide, nitrile, and/or nitro functional groups.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

It has been discovered that a solid, heterogeneous hydrogenation catalyst that can be substantially free of metals (i.e., that is "metal-free") or not, can be made from a solid material having a surface with both Lewis acid and Lewis base sites. While not intending to be limited to the chemical mechanism involved, it is believed that the introduction of a defect into the solid material "frustrates" a pair of Lewis acid and Lewis base sites resulting in an active hydrogenation catalyst that can be used in a heterogeneous catalyst system. It is believed that the FLPs create a catalytically active surface functionality that permits chemisorption of hydrogen and chemisorption of a compound containing sp-hybridized carbon and/or $sp^2$-hybridized carbon with a structure sufficient to allow chemisorption and subsequent reaction (e.g., hydrogenation) to take place. For example, but without limitation, the compound containing sp-hybridized carbon and/or $sp^2$-hybridized carbon is a compound comprising one or more carbonyl groups.

In one embodiment of the heterogeneous hydrogenation catalyst, it has been found that hexagonal boron nitride (h-BN) can produce a heterogeneous FLP under certain novel and non-obvious modifications. Hexagonal boron nitride (h-BN) can be described as a honeycomb network of fused borazine rings. The sheets of h-BN are loosely held together by van der Waals interactions between adjacent boron and nitrogen atoms, which stack in an ABAB fashion.

Figure 1:
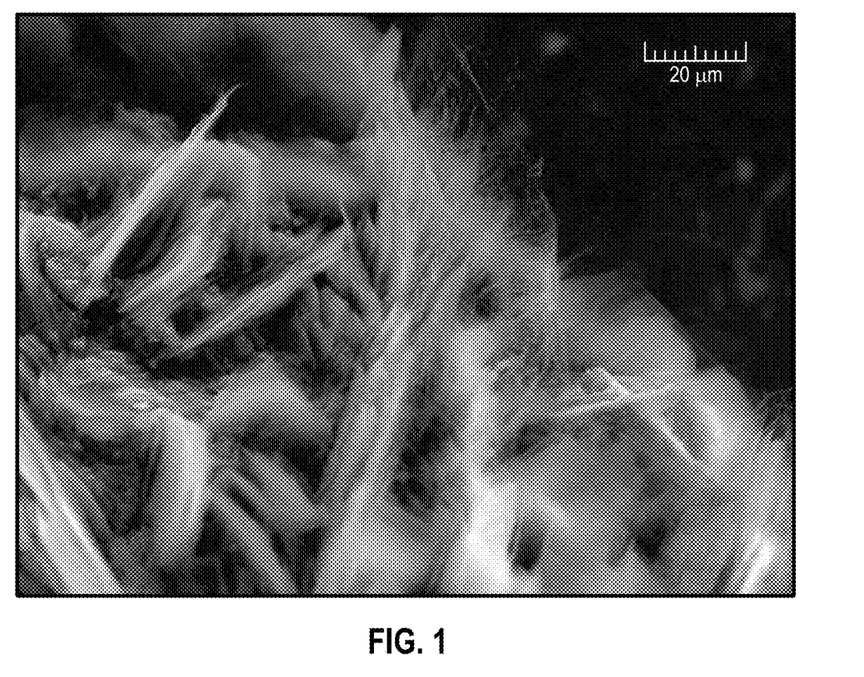
FIG. 1 is a SEM image of defect laden h-BN.

Pristine sheets of h-BN are exceptionally robust and chemically inert. Hydrogen absorption on the surface of pristine h-BN is endothermic with respect to dissociation but may be enhanced by introducing vacancies or Stone-Wales-type defects into the h-BN sheet. Single layer hexagonal boron nitride sheets can also be thought of as a structurally frustrated Lewis pair. Through delamination and the introduction of other defects in the layers and structure of the materials, the degree of "frustration" within the h-BN molecule can be increased, thereby rendering the h-BN material catalytically active. Defects and delamination can be introduced through any known physical chemical, and/or electronic process. In one particular embodiment, such defects can be introduced through the application of mechanical force. When such defects are introduced, for example, the lone electron pairs on the nitrogen are free to interact with adjacent layers, but not with the adjacent boron itself. FIG. 1 illustratively depicts an example of defective laden h-BN.

As discussed further herein, such h-BN materials having defects giving rise to catalytic activity can be used as hydrogenation catalysts. The h-BN catalyst material, in particular but without limitation, can be used within any known reactor shape or type and may be used with or without a particular refractory material. In one particular embodiment, the h-BN catalyst material is particularly well-suited for use within a mechanical reactor (such as a mill) to catalyze hydrogenation. However, the heterogeneous catalysts described and/or claimed herein are not limited to use in a mechanical/mechanochemical reactor.

Density functional theory (DFT) calculations reveal a 0.56 electron transfer from B to N for defect-free h-BN sheets. (See Sattler, K. D. Handbook of Nanophysics. Functional Nanomaterials; Taylor & Francis: Boca Raton, 2011, hereby incorporated herein in its entirety). Defect-free h-BN behaves, at least theoretically, as an FLP. Computational studies also show that hydrogen absorption on the surface of defect-free h-BN is endothermic with respect to dissociation. Experimental studies have also shown that defect-free h-BN nanotubes can adsorb up to 2.6 mass % of hydrogen. (See Sattler, K. D. Handbook of Nanophysics. Functional Nanomaterials (2011)). As disclosed herein, the introduction of defects into the structural organization of h-BN results in a material having enhanced FLP structural defects on the surface of the h-BN material. After the introduction of such defects, the h-BN material exhibits catalytic activity and is capable of being used as a hydrogenation catalyst, for example. Density function theory (DFT) calculations have also previously suggested that carbon dioxide can be stored or activated on pyridine, electron-rich boron nitride, and on the $B_N$ defects in BN nanotubes (see Lim et al., Mechanism of Homogeneous Reduction of CO2 by Pyridine: Proton Relay in Aqueous Solvent and Aromatic Stabilization. Journal of the American Chemical Society, 2012. 135(1): p. 142-154; Ertem et al., Functional Role of Pyridiunium during Aqueous Electrochemical Reduction of CO2 on Pt(111). The Journal of Physical Chemistry Letters, 2013. 4(5): p. 745-458; and Sun et al., "Charge-Controlled Switchable $CO_2$ Capture on Boron Nitride Nanomaterials," Journal of the American Chemical Society, 2013. 135(22): p. 8246-8253, each of which is hereby incorporated by reference in their entirety), which possess similar electronic and structural motifs as defect-laden h-BN presently disclosed and/or claimed herein. As such, the defect-laden h-BN catalyst presently disclosed and/or claimed herein is capable of being a good hydrogenation catalyst for carbon dioxide.

Additionally, hydrogenation over stainless steel (i.e., through the use of a stainless steel catalyst) has recently been observed. (See F. Zhao, Y. Ikushima, M. Arai, "Hydrogenation of 2-butyne-1,4-diol to butane-1,4-diol in supercritical carbon dioxide." Green Chem. 5, 656 (2003)). In order to eliminate the possibility that the hydrogenation reactions using defect-laden h-BN catalyst material (as disclosed herein) were influenced or catalyzed by the stainless steel reactor components, exemplary catalysis reactions were performed using stainless steel components in the absence of defect laden h-BN catalyst material. Limited hydrogenation was observed when stainless steel milling media was utilized without the h-BN catalyst material—i.e., the stainless steel components contributions to catalytic activity were minor.

Figure 2:
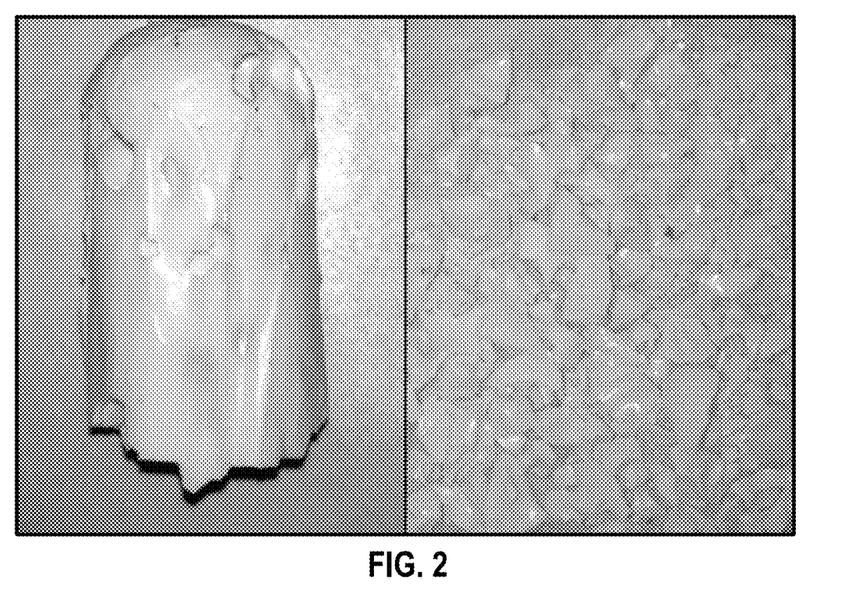
FIG. 2 is an image of a solid, porous structure of defect laden boron nitride dispersed in polydimethylsilazane obtained after heating under dynamic vacuum.

As disclosed, the controlled introduction of defects into h-BN produces a reliable and effective heterogeneous hydrogenation catalyst. In particular, but not by way of limitation, mechanical processing (e.g., grinding within a mill or through sonochemical processing) produces a defect-laden h-BN material that has catalytic activity—i.e., a heterogeneous hydrogenation catalyst. Mechanical processing may, in one embodiment, be required for the initial preparation of the defect laden h-BN. Grinding h-BN in the presence of hydrogen, for example, induced hydrogenation in a small batch reactor. However, hydrogenation over defect laden h-BN can be performed in a fixed bed reactor or other equipment known to those skilled in the art. For example, solid FLPs, including but not limited to h-BN, can be immobilized in oxygen-free polymers, such as polysilazanes, to produce materials suitable for fixed bed implementation, as illustrated in FIG. 2.

The presently disclosed and/or claimed heterogeneous hydrogenation catalyst is not limited to defect laden h-BN. Any solid structure containing a non-metallic Lewis acid type moiety and a non-metallic Lewis base type moiety can be used provided that the acid and base moieties are geometrically constrained so that an acid-base adduct cannot form. Non-limiting examples of suitable non-metallic Lewis acid type moieties include elements from Group 13 in a trigonal planar configuration; higher halides of Group 15 elements; and electron poor n-systems such as substitutionally doped graphite or carbon nitride. Non-limiting examples of suitable non-metallic Lewis base type moieties include simple anions such as fluoride and hydride; lone-pair-containing species such as Group 15 and Group 16 elements; complex anions such as sulfate, selenate, and tellurate; and electron rich n-system Lewis bases such as substitutionally doped graphite or carbon nitride. Examples of solids that would possess these properties include, but are not limited to, defect laden h-BN, substitutionally doped graphite, substitutionally doped carbon nitride, and inorganic-organic hybrid materials that contain both Lewis acid and Lewis base structures that are constrained from forming an acid-base adduct by the inorganic framework.

Without wishing to be held to any particular hypothesized mode of action, hydrogenation over the defect laden h-BN is believed to occur due to one or more of the following mechanisms: (i) through migration of protons over the catalyst surface, as observed in metal-catalyzed hydrogenation, (ii) through chemisorption of the reactant onto a protonated site, as observed in zeolite-catalyzed hydrogenation, and (iii) through the interaction of bound reactants on separate sheets of dh-BN. All of these mechanisms require the presence of defects for the initial chemisorption of hydrogen.

Figure 3:
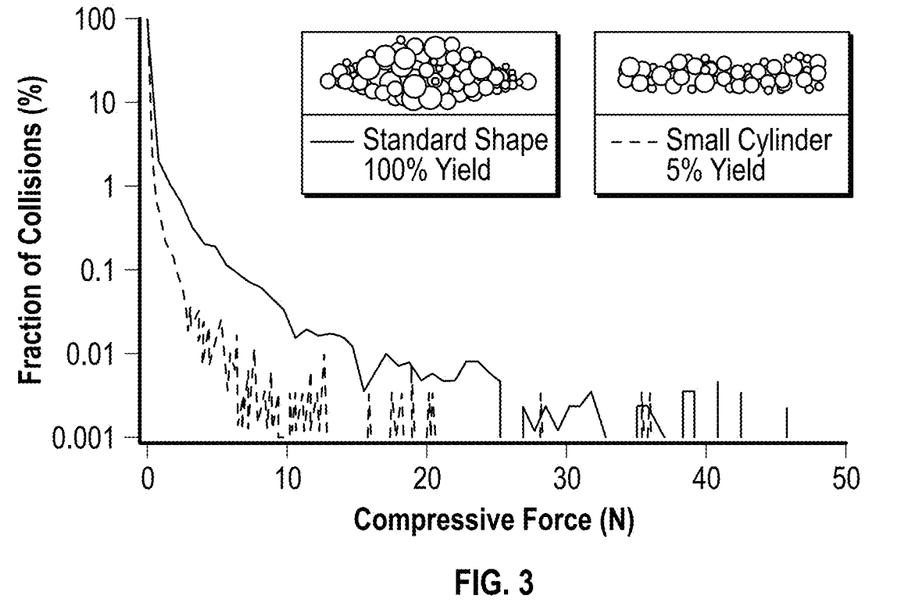
FIG. 3 is a graphical representation illustrating discrete element models that show that compressive forces achievable in our reactor are dependent on the milling intensity. The small cylinder utilized less media and had a smaller volume. This produced lower compressive forces and a lower hydrogenation yield (5% hydrogenation of chalcone after 24 hours). Higher forces are obtained using more media and a larger volume (standard shape). Improved hydrogenation was observed (100% hydrogenation of chalcone after 24 hours).

The first mechanism, i.e., hydrogenation through migration of protons over a catalyst, requires mobile defects in the catalyst since protons will be bound to the defect sites. The mobility of protons after hemolytic bond cleavage may proceed via a mechanism similar to the diffusion of hydrogen on a graphene sheet. See Herrero et al., "Vibrational properties and diffusion of hydrogen on grapheme," Phys. Rev. B: Condens. Matter Mater. Phys., 2009, 79(11): p. 115429/1-115429/8, hereby incorporated by reference in its entirety. Using a basic bond enthalpy analysis, this mechanism would require as much energy as diffusion of H on grapheme which proceeds by breaking and creation of C—H bonds (C—H, 337.2 kJ/mol, B—H 330 kJ/mol, N—H 339 kJ/mol) and be less favored when compared to nickel surfaces (Ni—H 289 kJ/mol). Additionally, the $V_N$ defects are not mobile but the $V_B$ defects are mobile above 840K and the B/N and Stone-Wales defects are mobile under plastic deformation. See Alem et al., "Vacancy growth and migration dynamics in atomically thin hexagonal boron nitride under electron beam irradiation." Physica Status Solidi Rapid Research Letter, 2011. 5(i): pp. 295-297; Zobelli et al., "Vacancy migration in hexagonal boron nitride," Phys. Rev. B: Condens. Matter Mater. Phys., 2007. 75(9): pp. 094104/1-094104/7; and Zhang et al., "Diffusion and coalescence of vacancies and interstitials in graphite: A first-principles study." Diamond & Related Materials, 2010. 19: pp. 1240-1244, each of which is hereby incorporated by reference in its entirety. The motion of defects in BN nanotubes has been observed under applied load and the forces generated during milling are sufficient to exceed the compressive yield strength of h-BN (41.3 MPa) when milling intensity is high enough (See FIG. 3);

The second mechanism, i.e., hydrogenation through chemisorption of the reactant onto a proton-laden defect, can occur without the application of mechanical force. Similar to the diffusion of protons over the dh-BN surface mechanism, as described above, no change in the catalytic efficiency would be expected when using dh-BN as a hydrogenation catalyst without the input of mechanical energy;

The third mechanism, i.e., hydrogenation through the interaction of bound reactants on separate sheets of dh-BN, can occur when a bound olefin on a dh-BN sheet interacts with a bound hydrogen on a separate dh-BN sheet when the two sheets come in close proximity due to mixing.

As mentioned, the presently disclosed and/or claimed inventive concept(s) has found that heterogeneous catalysts comprising a solid material having a surface with both Lewis acid and Lewis base sites with at least one defect are capable of reducing carbon dioxide to formic acid. In one embodiment, the heterogeneous catalyst is defect laden h-BN. Defect laden h-BN is useful as a heterogeneous catalyst because, as illustrated in Table 1, $H_2$ and $CO_2$ both have an affinity for the defects contained therein, specifically the boron rich defects. (See Choi, H., Y. C. Park, Y. H. Kim, and Y. S. Lee, *Ambient Carbon Dioxide Capture by Boron-Rich Boron Nitride Nanotube*. Journal of American Chemical Society, 2011, 133(7), pp 2084-2087, hereby incorporated in its entirety). The more negative the binding energy, the stronger the chemisorption of $H_2$ and $CO_2$ on the defective sites of the h-BN. Thus, both $CO_2$ and $H_2$ are activated in the presence of defect laden h-BN and the formation of formic acid results.

TABLE 1

| Surface Defects | Binding Energy (eV) | |
| --- | --- | --- |
| | Hydrogen | Carbon Dioxide |
| Boron Vacancy | −5.58 | — |
| Nitrogen Vacancy | −1.64 | — |

TABLE 1-continued

| Surface Defects | Binding Energy (eV) | |
| --- | --- | --- |
|  | Hydrogen | Carbon Dioxide |
| Stone-Wales Distortion | 0.64 | — |
| Nitrogen on Boron Site | 0.26 | — |
| Boron on Nitrogen Site | −2.16 | −0.34 |
| B/N swap | −8.66 | — |

The presently disclosed and/or claimed invention is also directed to a method of collecting hydrocarbons indirectly produced using the above-described heterogeneous catalysts, wherein the catalysts are coated with at least one or more hydocarbon during the reduction of $CO_2$. In one embodiment, the at least one or more hydrocarbon is removed from the catalyst by heating the catalyst to a temperature greater than about 100° C., or greater than about 400° C., or greater than about 800° C., and collected by condensation.

As such, the presently disclosed and/or claimed heterogeneous catalysts can be used to chemically reduce $CO_2$ using relatively low temperatures and relatively low amounts of energy. The presently disclosed and/or claimed inventive concept(s) encompasses the use of heterogeneous hydrogenation catalysts for the reduction of $CO_2$ and the production of formic acid and the indirect formation of hydrocarbon byproducts, which together have a significant commercial and environmental value.

Examples

In one exemplary embodiment, a hydrogenation reactor can be constructed in a manner similar to a pebble mill. Such a pebble mill is capable of producing defect laden h-BN by mechanically inducing defects and delamination of the physical structure of h-BN. The continuous grinding motion within the mill prevents cluster formation and maximizes the number of few-layer sheets of h-BN. In order to verify the presence of defect-laden sheets, scanning electron microscopy (SEM) was used to characterize the morphology of the defect laden h-BN catalyst. Few-layer sheets are observed by SEM and appear to form tubular structures or nanoscrolls as seen in FIG. 1.

The application of mechanical force is, in one embodiment, a preferred method for the delamination and formation of defects in the h-BN catalytic material. Such a delaminating and defect forming force can be applied during the step of hydrogenation or may be utilized as a pretreatment step since the defect sites are stable up to 900° C. (See, P. Wang, S. Orimo, T. Matsushima, H. Fujii, G. Majer, "Hydrogen in mechanically prepared nanostructured h-BN: a critical comparison with that in nanostructured graphite." Applied Physics Letters 80, 318 (2002)). The application of force during milling requires the efficient transfer of mechanical force to the h-BN catalyst material.

Synthesis of Defect Laden h-BN

Figure 4:
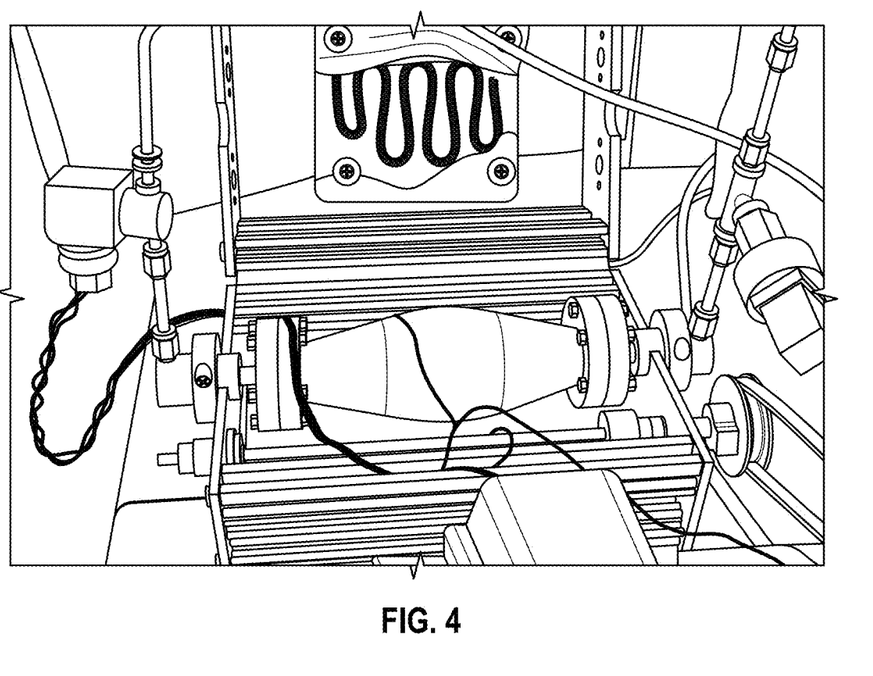
FIG. 4 is an illustration of a mechanical reactor for the reduction of $CO_2$ to formic acid.
Figure 8:
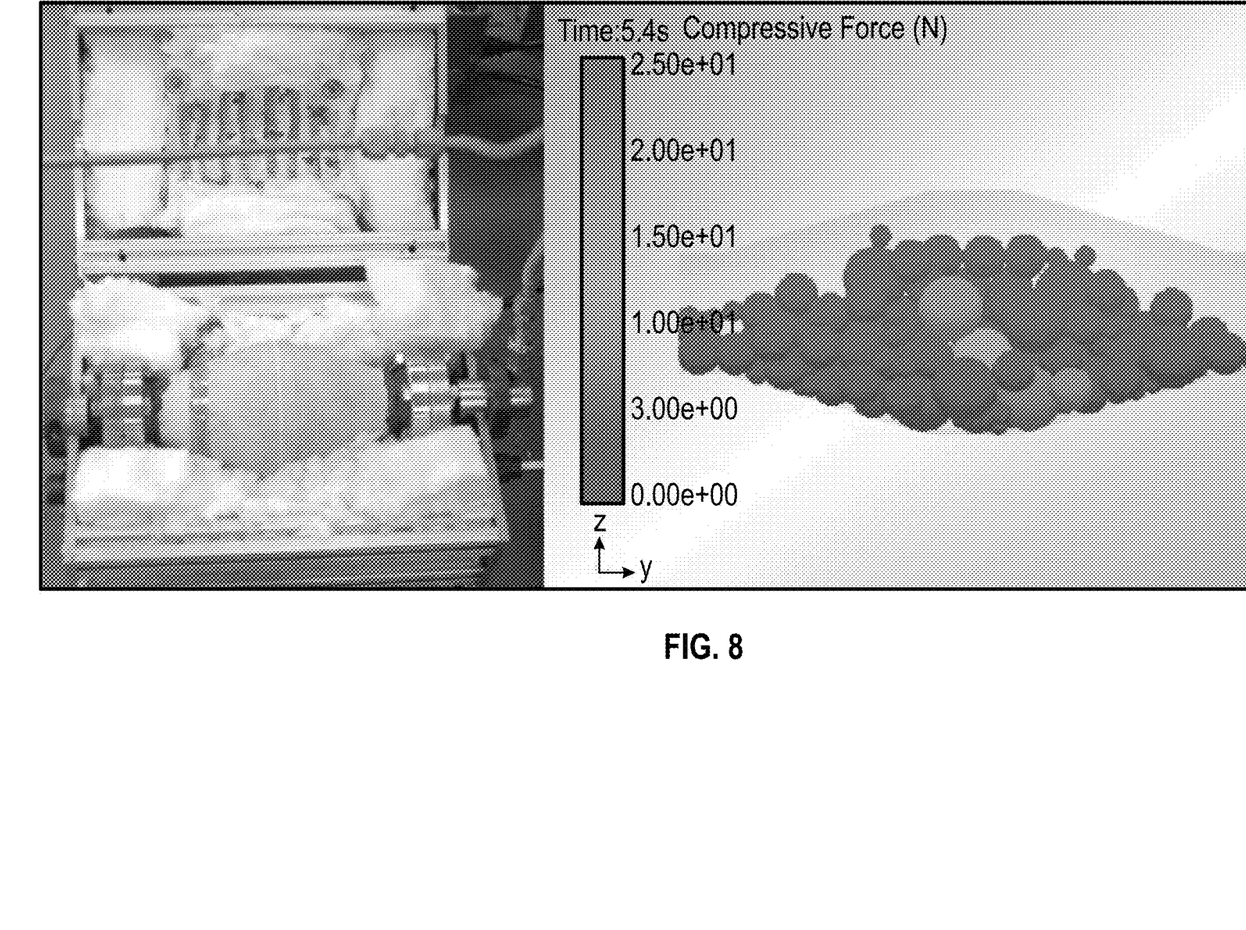
FIG. 8 (left) is an image of a pebble mill reaction vessel constructed of alumina and filled with $ZrO_2$ milling media. The sloped sides facilitate circulation of the catalyst. (Right) A simulation of the reactor shows the evolution of forces that occur. At 66 rpm, forces up to 25 N are realized.

Defect laden h-BN was synthesized by the application of mechanical force to h-BN under hydrogen for 96 hours in a custom pebble mill, hereafter described in detail, with a gas-tight milling container constructed of 304 stainless steel (see FIG. 4). The reaction vessel was shaped as a double truncated cone to ensure adequate tumbling of the milling media. Conflat flanges with silicone O-rings and Deublin® rotary feedthroughs (Deublin Company, Waukegan, Ill.) with Kalrez® O-rings (E.I. du Pont de Nemours and Company, Wilmington, Del.) and Krytox® lubricant (E.I. du Pont de Nemours and Company, Wilmington, Del.) were used to maintain gas tight conditions during operation. Stainless steel frits (Applied Porous Materials) were fitted to the entry and exit feedthroughs to eliminate the accumulation of dust in the sealing surfaces of the feedthroughs. Spherical milling media (440C) was added in the following quantities: twelve 0.75" balls, sixty-three 0.5" balls, and eighty-six 0.25" balls. Temperature was controlled with an Omega® CN3000 process controller (Omega Engineering Inc, Stamford, Conn.) and a K-type thermocouple spring mounted to the inlet flange. Heat was applied by a wound NiChrome heating element embedded in shaped firebrick. Pressure was monitored with a NOSHOK® (NOSHOCK, Inc., Berea, Ohio) pressure transducer and controlled with a MICROMOD 53MC5000 loop controller (MicroMod Automation & Controls, Rochester, N.Y.). The mill's rotational speed was controlled with a ⅓hp variable speed DC motor. An alternative custom pebble mill that may be used to synthesize defect laden h-BN, similar to the one made out of stainless steel described above, was constructed out of alumina and used $ZrO_2$ milling media (FIG. 8).

Hydrogenation

Figure 5:
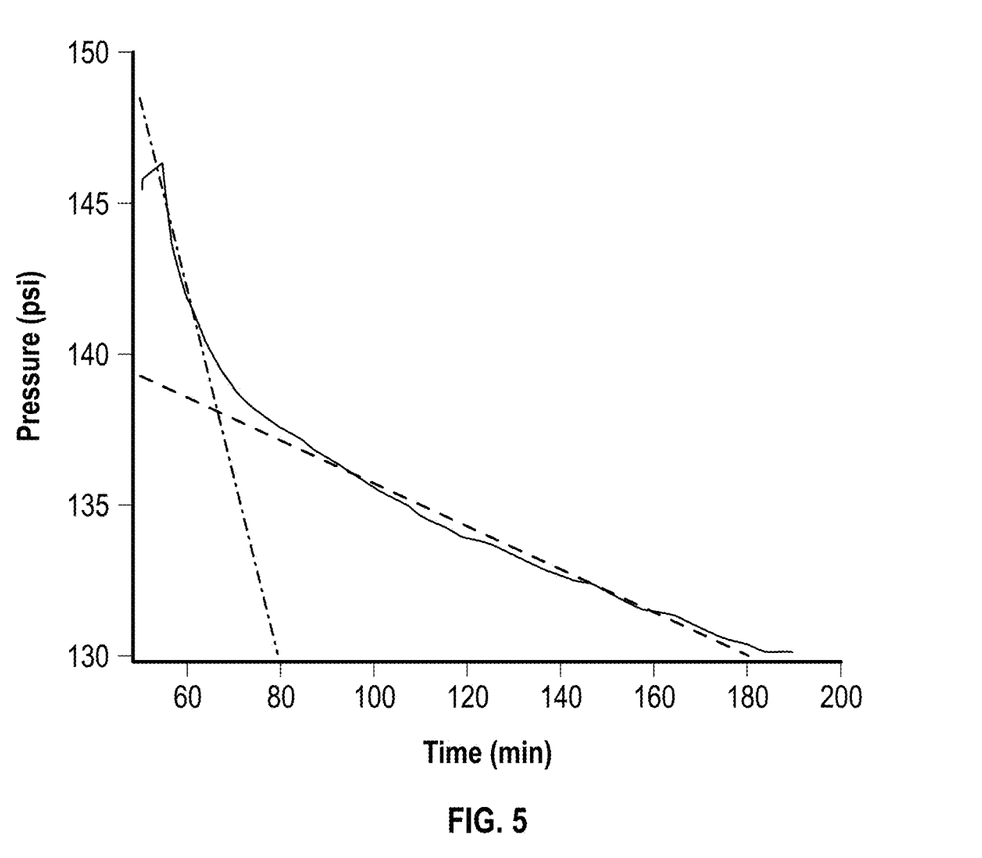
FIG. 5 is a graphical representation of the rapid pressure loss (dashed and dotted line) measured at 170° C. resulting from the production of formic acid and its subsequent trapping as a liquid in an activated charcoal coal trap.

Hydrogenation (also referred to herein as a "reduction reaction") was performed in the custom pebble mill described above for the synthesis of defect laden h-BN. The hydrogenation reactions were carried out at temperatures up to 170° C., pressures between 150 and 120 psi, and a rotary speed of 60 rpm. Hydrogenations were performed with 2 grams of the defect laden h-BN catalyst and a starting pressure of 60 psi of $CO_2$ and 60 psi of hydrogen. Additionally, since formic acid boils at 100.8° C., a cold trap consisting of a Hoke® tee filter (Hoke Inc., Spartanburg, S.C.) with a stainless steel frit filled with activated charcoal was added to the outlet to absorb the formic acid produced. The tee was kept at 4° C. using a Thermotek® recirculating chiller (ThermTek, Inc., Flower Mound, Tex.). FIG. 5 illustrates the pressure profile of the reactor over time and depicts the rapid pressure loss measured when the reactor reached 170° C. due to the production of formic acid and its subsequent trapping in the activated charcoal cold trap.

Gas Chromatography with Mass Sensitive Detection

Figure 6:
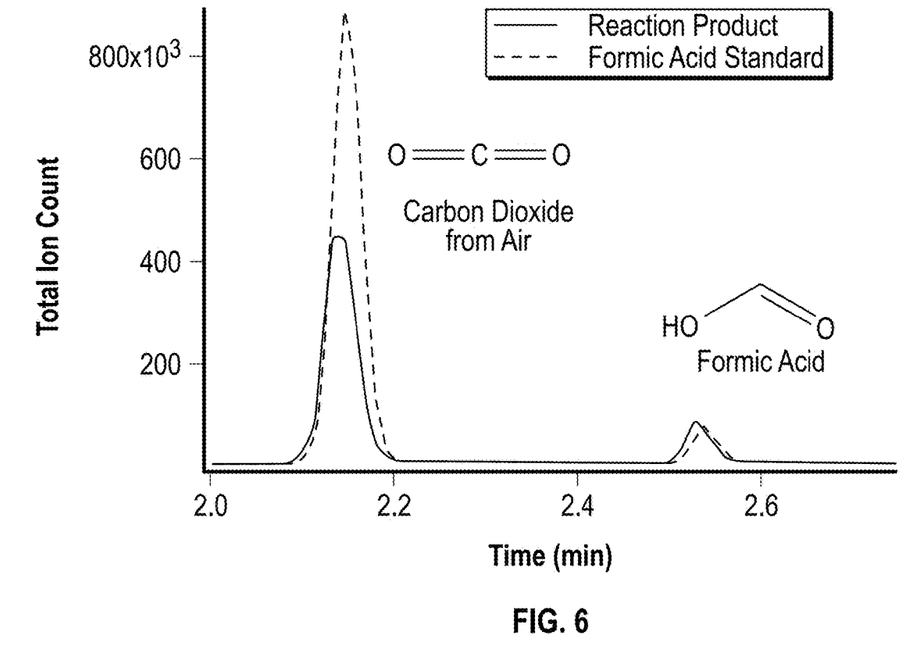
FIG. 6 is a graphical representation showing the formation of formic acid from the reduction of carbon dioxide.
Figure 7:
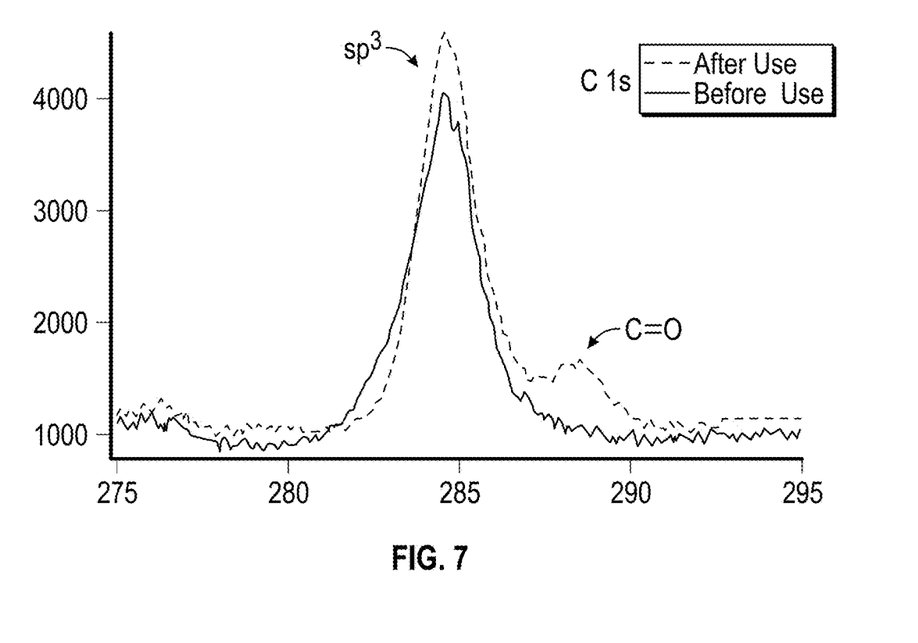
FIG. 7 is a graphical representation showing the incorporation of carbon onto defect laden h-BN catalyst after using the catalyst to reduce $CO_2$ into formic acid.

GC-MS analysis was performed on an Agilent 6850 GC (Agilent Technologies, Santa Clara, Calif.) with an Agilent 19091-433E HP-5MS column (5% phenyl methyl siloxane, 30 m×250 μm×0.25 μm nom.) coupled with a 5975C VL mass selective detector. Activated charcoal samples were removed from the filter tee and placed in a 10 mL sealed GC headspace container. The containers were heated to 150° C. and 2 μL of the headspace gas was sampled. The results of the analysis depicted in FIGS. 6 and 7 illustrate the formation of formic acid (FIG. 6) and the incorporation of carbon onto the h-BN catalyst represented as carbonyl structures (FIG. 7).

XPS

Figure 9:
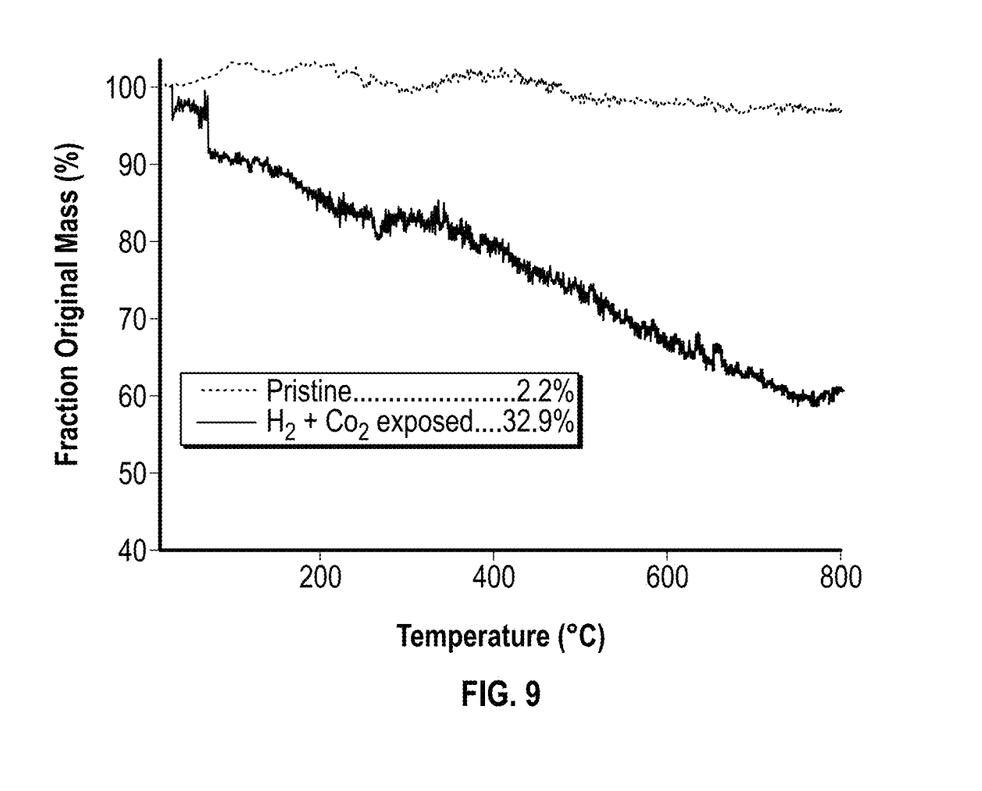
FIG. 9 is a graphical representation of the thermogravimetric analysis, in air, of the catalyst before (dashed line) and after (solid line) the reduction of carbon dioxide. As illustrated, significant amounts of carbon compounds are immobilized on the catalyst.
Figure 10:
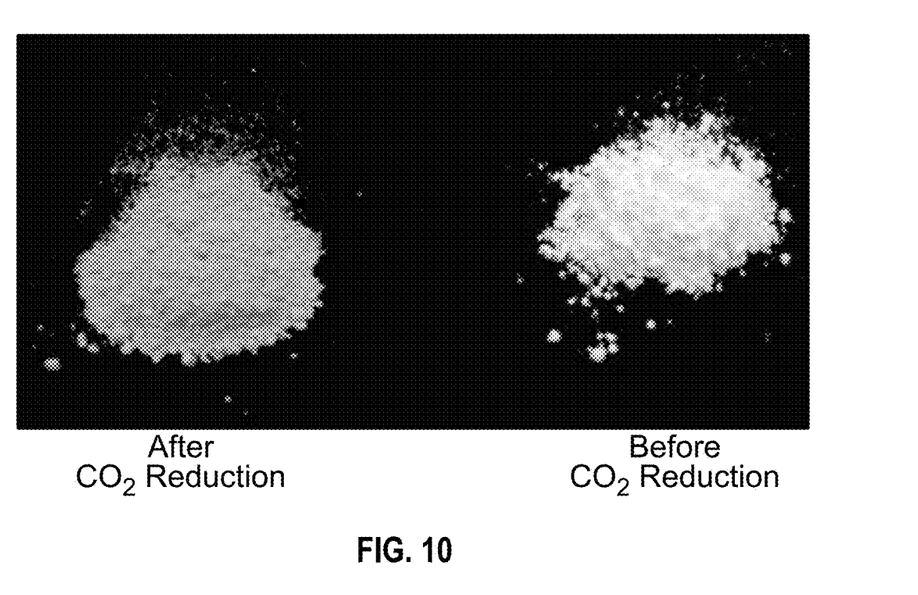
FIG. 10 is an image illustrating that carbon is incorporated onto the defect laden h-BN catalyst after the reduction of carbon dioxide, which results in the catalyst turning a tan or brown shade (left side of image).

The incorporation of carbon onto the catalyst was measured using X-ray photoelectron spectra (XPS) analysis and TGA analysis, whereby the XPS analysis confirmed that carbon was in fact bound to the dh-BN surface and the TGA analysis indicated a capture of approximately 32.9 mass percent carbon (FIG. 9). The XPS analysis was done using a Physical Electronics 5400 photoelectron spectrometer with a magnesium source, the results of which are presented in FIG. 7. Although the incorporation of carbon onto the catalyst turns the catalyst from a shade of white to a tan or brown (FIG. 10), the catalytic ability of the defect laden h-BN is not affected.

Collection of Hydrocarbons Produced by the Incorporation of Carbon onto the Catalyst The catalyst was regenerated by heating the catalyst in air to 800° C., returning the color of the catalyst to white. It is anticipated, and would be understood to one of ordinary skill in the art to be disclosed herein, that other methods exist to remove the carbon-based compositions from the catalyst including, for example but without limitation, oxidizing it to CO. While heating the catalyst, the carbon-based compositions incorporated onto the catalyst were removed from the surface of the catalyst and collected by condensation and thereafter determined to comprise carbon in the form of hydrocarbons. As such, the controlled introduction of defects into h-BN produces a reliable and effective $CO_2$ reduction catalyst that is also capable of producing hydrocarbons from $CO_2$.

From the above description, it is clear that the inventive concept(s) disclosed herein is well adapted to carry out the objects and to attain the advantages mentioned herein as well as those inherent in the inventive concept(s) disclosed herein. While exemplary embodiments of the inventive concept(s) disclosed herein have been described for purposes of this disclosure, it will be understood that numerous changes may be made which will readily suggest themselves to those skilled in the art and which are accomplished without departing from the scope of the inventive concept(s) disclosed herein and defined by the appended claims.

What is claimed is:

1. A hydrogenation process, comprising:
catalytically hydrogenating a compound having at least one functional group selected from the group consisting of carbonyls, nitriles, alkenes, alkynes, and combinations thereof, with a catalyst comprising a solid material comprising a sheet of catalytically active material having frustrated Lewis acid-base pairs along a surface of the sheet.

2. The process of claim 1, wherein the compound comprises at least one carbonyl group.

3. The process of claim 2, wherein the compound is carbon dioxide.

4. The process of claim 3, wherein the hydrogenation of carbon dioxide produces formic acid.

5. The process of claim 1, wherein the solid material having frustrated Lewis pairs comprises a solid surface having at least one Lewis acid site and at least one Lewis base site, and at least one defect frustrating at least one pair of Lewis acid and Lewis base sites, wherein the at least one frustrated pair of Lewis acid and Lewis base sites is catalytically active.

6. The process of claim 1, wherein the solid material having frustrated Lewis pairs comprises a solid surface having Lewis acid moieties and Lewis base moieties spaced a distance apart from one another such that catalytic activity is present there-between and the formation of an acid-base adduct therefrom is prevented.

7. The process of claim 6, wherein the Lewis acid moieties are selected from the group consisting of Group 13 elements in a trigonal planar configuration, halides of Group 15 elements, electron poor π-systems, and combinations thereof.

8. The process of claim 6, wherein the Lewis base moieties are selected from the group consisting of simple anions, lone-pair-containing species, complex anions, electron rich π-systems, and combinations thereof.

9. The process of claim 6, wherein the Lewis acid moieties are selected from the group consisting of Group 13 elements in a trigonal planar configuration, halides of Group 15 elements, electron poor π-systems, and combinations thereof, and the Lewis base moieties are selected from the group consisting of simple anions, lone-pair-containing species, complex anions, electron rich it-systems, and combinations thereof.

10. The process of claim 6, wherein the Lewis acid moiety is a Group 13 element in a trigonal planar configuration and the Lewis base moiety is a lone-pair containing species.

11. The process of claim 6, wherein the hydrogenation catalyst at least partially comprises hexagonal boron nitride.

12. The process of claim 1, wherein the catalyst comprises hexagonal boron nitride having a catalytically active defect on a surface thereof.

13. The process of claim 12, wherein the catalytically active defect is selected from the group consisting of Stone-Wales defects, B/N defects, boron substituted for nitrogen, nitrogen substituted for boron, carbon substituted for nitrogen, carbon substituted for boron, boron vacancy, nitrogen vacancy, and combinations thereof.

14. The process of claim 12, wherein the catalytically active defect is boron substituted for nitrogen.

15. The process of claim 1, wherein the compound has at least one functional group selected from the group consisting of carbonyls, nitriles, alkenes, and combinations thereof.

16. A hydrogenation process, comprising:
catalytically hydrogenating carbon dioxide with a catalyst comprising a solid material comprising a sheet of catalytically active material having frustrated Lewis pairs along a surface of the sheet, wherein the hydrogenation of the carbon dioxide coats at least one hydrocarbon onto the catalyst.

17. The process of claim 16, wherein the at least one hydrocarbon is collected by heating the catalyst to a temperature greater than 100° C.

18. The process of claim 17, wherein the catalyst is heated to a temperature greater than 400° C.

19. The process of claim 17, wherein the catalyst is heated to a temperature greater than 800° C.

* * * * *

UNITED STATES PATENT AND TRADEMARK OFFICE
CERTIFICATE OF CORRECTION

PATENT NO. : 10,329,233 B2
APPLICATION NO. : 15/472009
DATED : June 25, 2019
INVENTOR(S) : Richard G. Blair Page 1 of 1

It is certified that error appears in the above-identified patent and that said Letters Patent is hereby corrected as shown below:

In the Specification

Column 7, Line 40: Delete "n-systems" and replace with -- π-systems --

Column 7, Line 46: Delete "n-system" and replace with -- π-system --

In the Claims

Column 12, Line 18: Delete "it-systems," and replace with -- π-systems, --

Signed and Sealed this
Twenty-seventh Day of August, 2019

Andrei Iancu
*Director of the United States Patent and Trademark Office*